United States Patent [19]

Sheludyakov et al.

[11] 4,192,815

[45] Mar. 11, 1980

[54] METHOD OF PREPARING ISOCYANATES

[76] Inventors: Viktor D. Sheludyakov, ulitsa Metallurgov, 32, korpus 1, kv. 22, Moscow; Alexei D. Kirilin, VUGI, 9, kv. 23, Ljubertsy Moskovskoi; Vladimir F. Mironov, ulitsa Gubkina 4, kv. 13, Moscow; Sergei N. Glushakov, ulitsa Lenina 55, kv. 20; Yakov S. Karpman, ulitsa Lenina 55, kv. 32, both of Moskovskaya, all of U.S.S.R.

[21] Appl. No.: 918,824

[22] Filed: Jun. 22, 1978

[51] Int. Cl.² .................................................. C07C 118/00
[52] U.S. Cl. ............................ 260/453 P; 260/448.2 B
[58] Field of Search ........................................ 260/453 P

[56] References Cited

U.S. PATENT DOCUMENTS 4,064,151   12/1977   Hedaya et al. ................... 260/453 P

*Primary Examiner*—Dolph H. Torrence
*Attorney, Agent, or Firm*—Haseltine, Lake & Waters

[57] ABSTRACT

A method of preparing organic isocyanates comprising interaction of primary amines and carbon dioxide with hexamethyldisilazane in the presence of an acidic catalyst at a temperature within the range of from 40° to 80° C. and decomposition of the resulting silyl esters of carbamic acid in the presence of a dehydration agent at a temperature within the range of from 0° to 350° C. The desired product is obtained with a yield of from 84 to 97% and the content of the principal compound of up to 99.9%.

Preparation of isocyanates by the method according to the present invention is not accompanied by the formation of wastes polluting the environments.

7 Claims, No Drawings

METHOD OF PREPARING ISOCYANATES

The present invention relates to methods of preparing organic isocyanates which are useful in the synthesis of compounds possessing physiologically active properties. Thus, methylisocyanate is used in the synthesis of 2,6-bis-(methylcarbaminoxymethyl)pyridine which is an active agent of an antisclerotic preparation known under the following trademarks: anginine (Japan), prodectine (Hungary), parmidine (USSR). Furthermore, methylisocyanate is used in the synthesis of α-naphthyl ester of methylcarbamine acid which is an active principle of a herbicidal preparation, viz., sevin. Cyclohexylisocyanate is the starting material in the preparation of dicyclohexylcarbodiimide employed as a stabilizing agent in polymeric compositions and as an auxiliary reagent in the organic synthesis.

BACKGROUND OF THE INVENTION

Known in the art are several methods for preparing isocyanates.

One of those methods comprises interaction of alkyl ethers of sulphuric or phosphoric acid with cyanates of metals. The yield of isocyanates is as high as 90% by weight. However, the starting ethers are rarely available and, in some cases, toxic compounds.

Exchange-type interaction of haloalkyls with silver cyanate is of interest only under laboratory conditions due to silver shortage. The method based on the addition of isocyanic acid to unsaturated compounds makes it possible to prepare only lower monoisocyanates.

The synthesis of monoisocyanates by carbonylation of amines is ineffective due to the use of equimolar amounts of rather expensive palladium chloride (E. Stern, M. L. Spector J. Org. Chem. 31,596, 1966).

Preparation of isocyanates by way of catalytic carbonylation of nitroalkyls requires high temperature within the range of from 100° to 250° C. and pressures of from 100 to 500 atm. The method of preparing isocyanates (with a yield of from 42 to 73%) by decomposition of N-formamides in the presence of chlorine-containing agents has not obtained practical application due to the multi-stage character of the process.

The classic method of preparing isocyanates by phosgenation of amines is complicated, since it necessitates the use of high temperatures and dehydrochlorinating agents. Phosgenation of alkylaminosilanes, in addition to the two-stage production process, necessitates the use of toxical phosgene.

Among phosgene-free methods the Kurcius method is a laboratory method due to the risk of explosion upon heating of inorganic and organic azides.

Also known in the art is preparation of a monoisocyanates by pyrolysis of esters of carbamic acid in the presence of $P_2O_5$ at a high temperature (100° to 500° C.), but due to the inversible character of the process, the product is obtained with a low yield.

Therefore, at the present time in the art there is a need in a suitable, versatile method for the preparation of said organic compounds.

OBJECT OF THE INVENTION

It is an object of the present invention to provide a versatile, one-stage, non-pollutant method for the preparation of organic isocyanates of a high purity and with a high yield.

SUMMARY OF THE INVENTION

In accordance with the present invention, a method of preparing organic isocyanates comprises reaction of primary amines with carbon dioxide and hexamethyldisilazane in the presence of an acidic catalyst at a temperature within the range of from 40° to 200° C. and the resulting silyl esters of carbamic acid are subjected to decomposition in the presence of a dehydration agent at a temperature within the range of from 0° to 350° C. Said esters are irreversible decomposed with the formation of a mixture of siloxanes, trimethylchlorosilane and monoisocyanates separated by conventional techniques.

The method according to the present invention makes it possible to obtain isocyanates with a high yield and a high purity grade.

Decomposition of silyl esters of carbamic acid occurs within a wide temperature range of from 0° to 350° C. However, for a more uniform and complete reaction, it is preferred to conduct the process at a temperature within the range of from 40° to 150° C. The process may be also conducted at a temperature above 350° C., but this necessitates sophisticated process equipment and the desired product yield becomes lowered; at temperatures below 0° C., the decomposition still takes place but it proceeds at a very slow rate.

As the dehydration agent use is made of $SOCl_2$, $PCl_5$, $AlCl_3$, silica gel, phenyltrichlorosilane.

DETAILED DESCRIPTION OF THE INVENTION

The method according to the present invention for preparing organic isocyanates is performed in the following manner.

Charged into a column-type reactor are hexamethyldisilazane, a primary amine and an acidic catalyst such as sulphuric acid. The reactor contents is heated at a temperature within the range of from 40° to 200° C. (depending on the starting components) and carbon dioxide is passed therethrough. Heating of the mixture is conducted till the reaction mixture refraction index is equal to a specified value corresponding to the silyl ester of carbamic acid being formed. The resulting silyl ester of carbamic acid produced in this reaction is drained, under stirring, into an apparatus provided with a stirrer, whereinto a dehydrating agent is already charged; without stopping the stirring, the mixture is heated at a temperature of from 20° to 350° C., preferably from 40° to 150° C. The resulting isocyanate is withdrawn by way of rectification under atmospheric or reduced pressure as it accumulates in the system.

The desired product is obtained at a yield of from 84 to 97% from the theoretical value and with the content of the principal compound of up to 99.9%.

The bottoms comprise a mixture of silanols and corresponding siloxanes which are used as the starting stock in the preparation of known surfactants or polysiloxane resins.

Said bottoms are liquid and readily removed from the reactor.

Therefore, the method according to the present invention has no harmful wastes, it is simple as to the process equipment, and may be easily implemented on a commercial scale.

The spent catalyst is readily regenerated and may be repeatedly used in the process.

As the acidic catalyst use is made of sulphocationites, phosphoric-acid cationites, as well as mineral acids or ammonium salts thereof.

The method according to the present invention has the following advantages:
- elimination of highly-toxic reagents such as phosgene or carbaminoylchlorides from the process;
- high yields of the desired products approaching 97% by weight;
- high purity of the resulting isocyanates suitable for use, after purification by a common rectification, in the manufacture of pharmaceutical preparations;
- moderate temperatures of the synthesis of isocyanates;
- possibility of performing the process under atmospheric or slightly reduced pressure;
- absence of wastes polluting the environments;
- the use of bottoms as a valuable stock in the manufacture of surfactants or polysiloxane resins.

The following Examples are given for a better understanding of the present invention.

EXAMPLE 1. Preparation of methylisocyanate

Into a reactor there are placed 11 kg of hexamethyl disilazane (HMDS) and 300 g of a catalyst, i.e. sulphocationite comprising a sulphonated organopolysiloxane, heated to a temperature of 65° to 70° C. and two gases are passed therethrough: methylamine and carbon dioxide till a refraction index of 1.4238–1,4242 is achieved. The resulting trimethylsilyl ester of methylcarbamic acid (OCY) under stirring is charged into an apparatus with a heating jacket, wherein 21 kg of phenyltrichlorosilane are already placed. The mixture is heated to the temperature of 145° C. and the final product, i.e. methylisocyanate (MIC) and trimethylchlorosilane (TMCS) in the amount of 11.1 kg is collected in a receiving vessel. The thus-prepared mixture is fractionated in a rectification column to give 3.6 kg of methylisocyanate (95% of the theoretical value) boiling at 38.5° C. and having $n_D^{20} = 1.3636$. (The content of the principal compound is equal to 99.9%).

The process parameters for other isocyanates prepared by the method according to the present invention as well as yields of the desired products are given in Table 1 hereinbelow.

The process parameters for other acidic catalysts are given in Table 2 hereinbelow.

Table 1

Process conditions and yields of the resulting isocyanates the presence of sulphonated polyorganosiloxane

| No. | Isocyanate prepared | Total time of the process, hrs | Amount of HDMS* charged, kg | Dehydrotion agent | Temperature, °C. Stage I | Temperature, °C. StaGE II | Yield, % Stage I CCY | Stage III MIC |
|---|---|---|---|---|---|---|---|---|
| 1. | Methylisocyanate | 8.0 | 46 | C$_6$H$_5$SiCl$_3$ | 65–70 | 145 | 96 | 92 |
| 2. | Methylisocyanate | 8.5 | 45 | SiCl$_4$ | 65–70 | 140 | 98 | 94 |
| 3. | Methylisocyanate | 8.5 | 45 | SOCl$_2$ | 65–70 | 140 | 96 | 92 |
| 4. | Allylisocyanate | 6.5 | 35 | C$_6$H$_5$SiCl$_3$ | 35–45 | 147 | 98 | 93 |
| 5. | Allylisocyanate | 7.0 | 30 | SiCl$_4$ | 35–45 | 146 | 96 | 93 |
| 6. | n-butylisocyanate | 7.0 | 24 | C$_6$H$_5$SiCl$_3$ | 45–55 | 146 | 96 | 92 |
| 7. | iso-butylisocyanate | 7.5 | 26 | SiCl$_4$ | 40–50 | 145 | 97 | 93 |
| 8. | cycloxehylisocyanate | 8.0 | 21 | C$_6$H$_5$SiCl$_3$ | 55–60 | 146 | 97 | 90 |

*HMDS - hexamethyldisilazane

Table 2

Process conditions in the systhesis of methylisocyanate

| No. 1 | Catalyst 2 | Catalyst amount, % by weight of HMDS* 3 | Synthesis time, hrs 4 | Temperature, °C. 5 | Pressure atm.g. 6 | Product yield, % OCY* 7 | Product yield, % MIC* 8 | Product yield, % TMCS* 9 |
|---|---|---|---|---|---|---|---|---|
| | Sulphocationites | | | | | | | |
| 1. | Sulphonated copolymer of n-quinone with formaldehyde | 3.5 | 12–14 | 65–90 | 0.01–1.0 | 93.0 | 91.0 | 94.7 |
| 2. | Sulphonated styrenedivinylbenzene copolymer | 4.0 | 8–12 | 60–90 | 0.2–40.0 | 96.0 | 94.0 | 96.2 |
| 3. | Sulphonated vinylnaphthalene-divinylbenzene copolymer | 5.0 | 10–12 | 65–85 | 0.01–1.0 | 94.0 | 95.0 | 97.1 |
| 4. | Sulphonated acenapthylene-divinylbenzene copolymer | 5.0 | 8–11 | 65–95 | 0.01–1.0 | 87.2 | 91.1 | 92.9 |
| 5. | Sulphonated resin based on acenaphthylene and formaldehyde | 5.0 | 8–11 | 65–95 | 0.01–0.5 | 82.4 | 94.3 | 98.8 |
| 6. | Resin based on phenolsulphonic acid, formaldehyde and other aliphatic aldehydes. | 6.0 | 12–15 | 60–95 | 0.01–0.5 | 89.8 | 95.6 | 98.6 |
| 7. | Resin based on haphthalenesulphonic acid and formaldehyde | 6.0 | 10–14 | 55–100 | 0.01–60.0 | 90.7 | 95.4 | 98.1 |
| 8. | Sulphonated polyorganosiloxane | 5.0 | 5–10 | 50–95 | 0.01–40.0 | 95.6 | 95.3 | 99.4 |

Table 2-continued

Process conditions in the systhesis of methylisocyanate

| No. | Catalyst | Catalyst amount, % by weight of HMDS* | Synthesis time, hrs | Temperature, °C. | Pressure atm.g. | Product yield, % | | |
|---|---|---|---|---|---|---|---|---|
| | | | | | | OCY* | MIC* | TMCS* |
| 1 | 2 | 3 | 4 | 5 | 6 | 7 | 8 | 9 |
| 9. | Sulphonated styrene-butadiene copolymer | 4.0 | 4-6 | 50-95 | 0.01-100.0 | 95.7 | 96.1 | 98.0 |
| 10 | Para chlorobenzenesulphonic acid-formaldehyde copolymer | 4.0 | 12-18 | 65-90 | 0.01-0.2 | 91.8 | 94.4 | 96.4 |
| 11 | Sulphonated napthalene-formaldehyde copolymer | 5.0 | 10 | 70-85 | 0.01-0.7 | 90.8 | 95.2 | 99.8 |
| | Phosphoric-acid cationites | | | | | | | |
| 12 | Resin based on polyvinyl alcohol | 5.0 | 8-14 | 80-95 | 0.01-25.0 | 89.2 | 96.8 | 99.0 |
| 13 | Resin based on polystyrene | 5.0 | 8-14 | 70-95 | 0.01-57.0 | 80.2 | 95.4 | 99.1 |
| 14 | Resin based on phenol and resorcinol | 5.0 | 8-12 | 70-95 | 0.01-74.0 | 82.4 | 94.5 | 99.6 |
| | Other catalysts | | | | | | | |
| 15 | Concentrated sulphuric acid | 3.0 | 8-18 | 65-95 | 0.01-10.0 | 94.1 | 96.0 | 97.1 |
| 16 | Concentrated phosphoric acid | 3.0 | 8-18 | 65-95 | 0.01-10.0 | 93.0 | 94.6 | 96.4 |
| 17 | Bis-(trimethylsilyl)sulphate | 4.0 | 8-16 | 65-90 | 0.01-10.0 | 96.2 | 95.1 | 97.3 |
| 18 | Trimethylsilylphosphate | 4.0 | 8-16 | 65-90 | 0.01-10.0 | 92.3 | 96.4 | 97.2 |
| 19 | Ammonium sulphate | 4.0 | 8-15 | 65-95 | 0.01-10.0 | 94.7 | 97.3 | 97.0 |
| 20 | Ammonium carbamate | 1-9 | 8-20 | 65-95 | 0.01-10 | 88.7 | 94.6 | 96.1 |
| 21 | Trimethylchlorosilane | 10 | 8-20 | 65-95 | 0.1-25.0 | 72.3 | 95.1 | 98.8 |
| 22 | Phenyltrichlorosilane | 5 | 8-20 | 40-195 | 0.01-25.0 | 75.4 | 96.1 | 99.0 |
| 23 | Silicon tetrachloride | 4 | 18-20 | 40-160 | 0.01-25.0 | 78.1 | 96.3 | 99.2 |
| 24 | Sulphonated coal | 5 | 18-20 | 60-160 | 0.01-0.15 | 56.0 | 92.7 | 98.0 |
| 25 | Sulphoorganylpolysiloxane on SiO$_2$ | 5 | 3-16 | 60-100 | 0.01-100.0 | 96.0 | 96.6 | 96.6 |

*HMDS - hexamethyldisilazane:
OCY - trimethylsilyl ester of methylcarbamic acid;
MIC - methylisocyanate;
TMCS - trimethylchlorosilane.

What is claimed is:

1. A method of preparing organic isocyanates comprising interaction of primary amines having 1 to 6 carbon atoms and carbon dioxide with hexamethyldisilazane in the presence of an acidic catalyst selected from mineral acids, organic acids or salts thereof, sulfocationites or phosphoric acid cationites, at a temperature within the range of from 40° to 200° C. and subsequent decomposition of the resulting silyl esters of carbamic acid in the presence of a dehydration agent at a temperature within the range of from 0° to 350° C.

2. A method according to claim 1, wherein decomposition of said silyl esters is conducted at a temperature within the range of from 40° to 150° C.

3. A method according to claim 1, wherein as the catalyst use is made of an ion-exchange resin.

4. A method according to claim 1, wherein as the catalyst use is made of mineral acids or ammonium salts thereof.

5. A method according to claim 1, wherein as the catalyst use is made of sulphonated polyorganosiloxanes.

6. A method according to claim 1 wherein the acid catalyst is sulfuric acid, phosphoric acid, bis-(trimethylsilyl)sulfate, trimethylsilylphosphate, ammonium sulfate, ammonium carbamate, trimethylchlorosilane, phenyltrichlorosilane, silicon tetrachloride, sulfonated coal, sulfoorganylpolysiloxane on SiO$_2$, sulfonated copolymer of n-quinone and formaldehyde, sulfonated styrene-divinylbenzene copolymer, sulfonated vinylnaphthalenedivinylbenzene copolymer, sulfonated resin based on acenaphthylene and formaldehyde, resin based on phenolsulfonic acid, formaldehyde and other aldehydes, resin based on naphthalene sulfonic acid and formaldehyde, sulfonated polyorganosiloxane, sulfonated styrenebutadiene copolymer, para-chlorobenzenesulfonic acid-formaldehyde copolymer, sulfonated naphthalene-formaldehyde copolymer, and phosphoric acid cationites of resins based on polyvinyl alcohol, polystyrene or phenol and resorcinol.

7. A method according to claim 1 wherein said primary amine is a saturated, unsaturated, straight- or branched chain alkylamine, or cycloalkylamine.

* * * * *